United States Patent [19]

Stein et al.

[11] 4,314,970
[45] Feb. 9, 1982

[54] ANALYSIS SYSTEM

[75] Inventors: Bernard Stein, Andover, Mass.; Richard A. Granoff, Chester, N.H.

[73] Assignee: Instrumentation Laboratory Inc., Lexington, Mass.

[21] Appl. No.: 181,814

[22] Filed: Aug. 27, 1980

[51] Int. Cl.³ .................... G01N 21/07; G01N 21/09
[52] U.S. Cl. .................................. 422/72; 356/246; 422/64
[58] Field of Search ............... 422/72, 102, 104, 64; 356/246; 233/26

[56] References Cited

U.S. PATENT DOCUMENTS

| | | | |
|---|---|---|---|
| 3,798,459 | 3/1974 | Anderson et al. | 250/218 |
| 3,586,484 | 6/1971 | Anderson | 23/230 R |
| 3,759,666 | 9/1973 | Hill, Jr. | 23/230 B |
| 3,813,031 | 5/1974 | Anderson | 233/26 |
| 3,829,223 | 8/1974 | Hamel | 356/246 |
| 3,873,217 | 3/1975 | Anderson et al. | 422/72 |
| 3,899,296 | 8/1975 | Mailen et al. | 422/72 |
| 4,088,448 | 5/1978 | Lilja et al. | 356/246 X |
| 4,123,173 | 10/1978 | Bullock et al. | 422/64 |
| 4,226,531 | 10/1980 | Tiffany et al. | 356/246 |
| 4,256,696 | 3/1981 | Soodak | 422/72 |

Primary Examiner—Ronald Serwin

[57] ABSTRACT

A multicuvette rotor assembly for use in a clinical chemistry analyzer of the centrifugal type includes a body member that defines a circumferential array of spaced radially extending recesses, with a divider member in each recess to define a first chamber and a second chamber radial outward from said first chamber; and a ring member that has a mating reference surface seated on an annular reference surface of the body member, with the inner peripheral surface of the ring member located outwardly of the middle of the second chambers. A circumferential array of first optical windows is bonded to the ring member, the lower surface of each first optical window being parallel to the mating reference surface; and a circumferential array of second optical windows is bonded to the base of the body member in alignment with the first optical windows such that each pair of opposed aligned surfaces of corresponding first and second optical windows are parallel to one another and define an optical path of precise and stable path length. A cover member has sealing surfaces that mate with the edges of the recesses of the base member and the inner peripheral lip of the ring member to provide a continuous seal of the recesses to retain reagent and sample material to be analyzed within the recesses.

17 Claims, 16 Drawing Figures

ANALYSIS SYSTEM

This invention relates to analytical instruments and more particularly to multicuvette rotor assemblies for use in centrifugal analyzers of the photometric type, and to similar precision assemblies.

Centrifugal analyzers are useful in performing kinetic and end point analyses. In general, such analyzers have utilized a multicuvette rotor assembly which has a plurality of radially disposed cuvettes that extend outwardly from a central hub with an annular series of inner chambers for initially holding a first group of reactants, an annular series of divider structures such as ramps, and an annular series of outer chambers for initially holding different reactants which are frequently unknown samples of blood or other biological fluid. A pair of spaced optical windows in each second or outer chamber defines an optical path of precise length for use in the photometric measurement. The rotor is usually driven at a preliminary fast speed in the vicinity of 3000–5000 rpm in which the reactant in each inner chamber flows over the divider and mixes with the reactant in the outer chamber, and then during a measurement run at speeds of approximately 1000 rpm. The temperature of the rotor is closely controlled as temperature affects reaction rates and light transmission characteristics change as reactions proceed.

The most common use of such analyzers is in the determination of blood or blood plasma or serum components, and the chemistry procedures that are performed include but are not limited to analyses for glucose, cholesterol, creatinine, total protein, calcium, phosphorus, and enzymes. Several of the reagents used in such analyses are quite reactive, and therefore the rotor assembly must be corrosion resistant, as well as being well sealed. It is essential that the rotor have precise and stable dimensional accuracies to achieve the desired analysis accuracies, particularly where the cuvette volumes are small (in the order of microliters). Prior art multicuvette rotors in general have been either relatively complex assemblies that are expensive to manufacture and difficult to clean, or disposable (single use) rotors.

In accordance with the invention there is provided a multicuvette rotor for use in an analytical system of the centrifugal type that includes a body member in which a circumferential array of upwardly open cuvette recesses are defined, with divider structure in each cuvette recess such that each recess defines a first chamber and a second chamber radially outward from the first chamber. Around the periphery of the body member are a series of radially extending reference surface areas and seated in face-to-face contact on those reference surfaces are corresponding reference surface areas of a ring member such that the ring member overlies outer portions of the second chambers with its inner peripheral edge located outwardly of the middle of the second chambers. The ring member includes a circumferential array of first optical windows, the lower surfaces of which are parallel to the reference surface areas of the ring. A corresponding series of second optical windows are in the floors of the second chamber portions of the cuvette recesses, with the upper surface of each second optical window parallel to the reference surface areas of the body member. The two series of optical windows are in alignment with one another so that there is defined in each second chamber an optical path of precise and stable path length between two parallel optical surfaces. A removable cover member has relatively soft conforming sealing surfaces that are adapted to overlie the walls of the cuvette recesses and the inner peripheral edge of the ring member and to sealingly enclose the individual cuvette chambers.

In accordance with another aspect of the invention, there is provided a bonding system in which reference surfaces of components to be bonded are in direct contact with one another, and a channel of capillary dimension (preferably less than 0.3 millimeter in width) is provided between the components to be bonded. A reservoir connected to the capillary channel receives a flowable bonding agent which has viscosity and surface tension characteristics such that the bonding agent flows from the reservoir into the capillary channel and fills but does not flow out of that channel. The bonding agent, preferably an epoxy resin provides a continuous sturdy, pore-free bond with a smooth, leak tight surface of excellent corrosion resistance.

In a preferred embodiment, there is provided an analysis cuvette assembly for use in an analytical system that comprises two members arranged to define an analytical chamber therebetween. Each member has a planar reference surface and those reference surfaces are in direct and mating engagement. A flowable bonding agent in a capillary channel between the two members provides a smooth surface of sturdy bond. Each chamber member also has an aperture in which there is a support surface parallel to and offset a predetermined distance from the reference surface of that member, and an optical window is seated on the support surface in each aperture such that its upper surface is offset at predetermined distance from the reference surface, and an annular channel of capillary dimension is defined between its peripheral surface and the adjacent aperture surface. A flowable bonding agent in that annular channel sets to provide a continuous and sturdy bond that secures each optical window in its aperture with the opposed surfaces of the optical windows being parallel to one another and defining an optical path of precise and stable path length.

In a particular embodiment both the body member and the ring member of a multicuvette rotor have seat areas on which optical windows of Pyrex glass are seated for accurate positioning. A capillary channel extends around the periphery of each optical window with a reservoir well immediately adjacent and in communication with the capillary channel. The base member has an annular aligning recess in which the ring member is seated such that the upper surface at the ring lies in the same plane as the upper surface of the body. Recesses in the ring member define capillary channel areas around the outer edges of the second cuvette chambers with reservoir apertures in communication with those channels. Epoxy resin bonding agents deposited in each reservoir flow from the reservoirs and fill the channels by capillary action to bond the optical windows to the base and ring members and to bond the base and ring members together.

The cuvette chambers of this reusable multicuvette rotor for a centrifugal analyzer are reliably sealed with a common cover member and are easily accessible for thorough cleaning. The epoxy bonding material fills crevices between the body and ring members and the optical windows and those members to provide smooth, easily cleaned surfaces. The ring and body members and the bonding agents are resistant to chemical attack from the reagents used in the chemical analysis and withstand the centrifugal forces to which the rotor is subjected during mixing and analysis sequences. The optical windows and the body ring members have a series of planar reference surfaces that are in direct mating contact with one another such that dimensionally accurate optical paths of the same length are defined in the circumferential array of cuvette chambers.

BRIEF DESCRIPTION OF THE DRAWINGS

Other features and advantages of the invention will be seen as the following description of a particular embodiment progresses, in conjunction with the drawings, in which.

DESCRIPTION OF PARTICULAR EMBODIMENT

Figure 1:
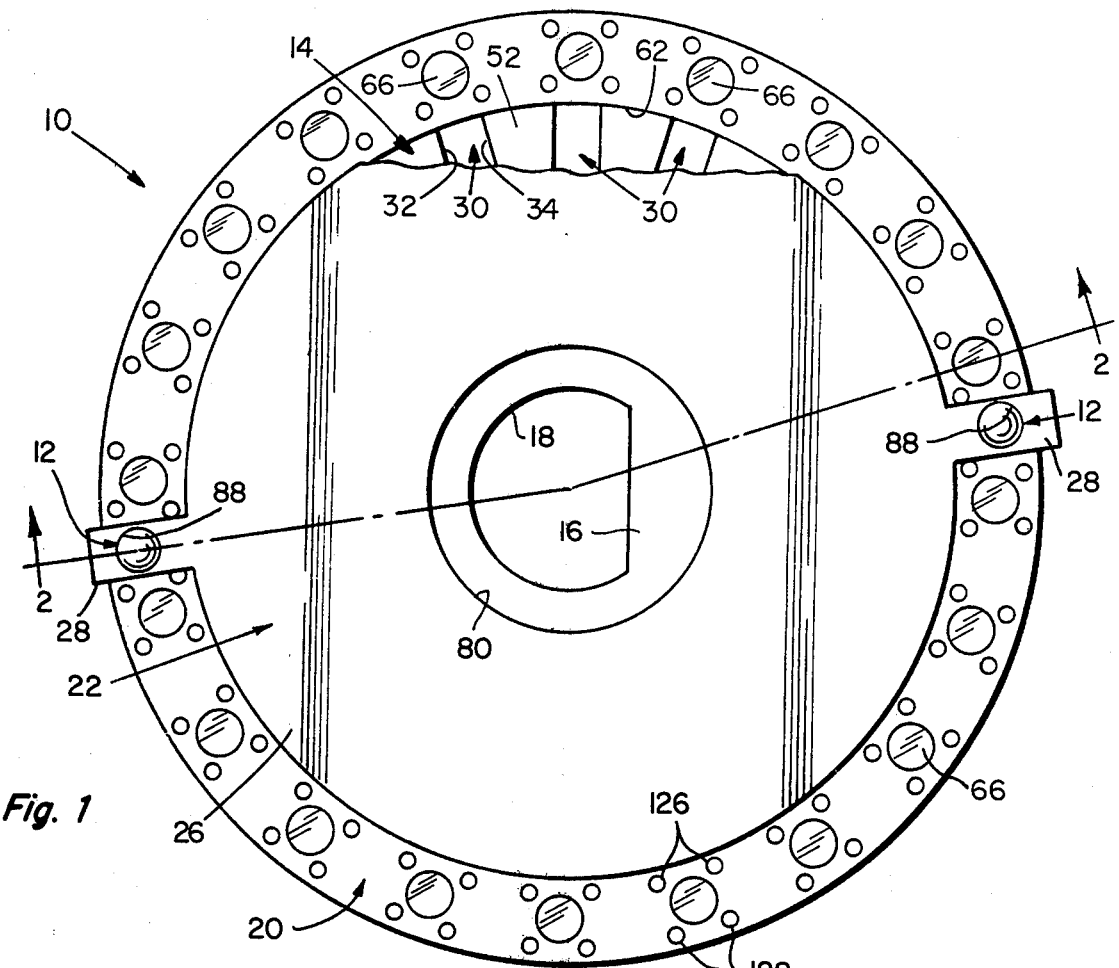
FIG. 1 is a top plan view of a multicuvette rotor assembly in accordance with the invention.
Figure 2:
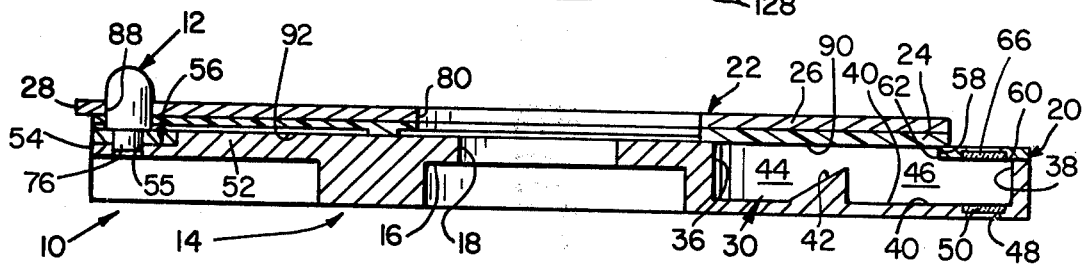
FIG. 2 is a sectional view taken along the line 2—2 of FIG. 1.

The rotor assembly 10 shown in FIGS. 1 and 2 has a diameter of about ten centimeters and an overall height (not including pilot posts 12) of about 1.2 centimeters. The rotor assembly includes a base member 14 which has a hub portion 16 in which is formed a generally D-shaped opening 18; a ring member 20 that is seated and bonded to an annular recess at the outer periphery of base member 14; and a removable cover assembly 22 that includes a gasket 24 bonded to pressure plate 26. Cover assembly 22 has radially extending tabs 28 that are piloted on pilot posts 12.

Figure 3:
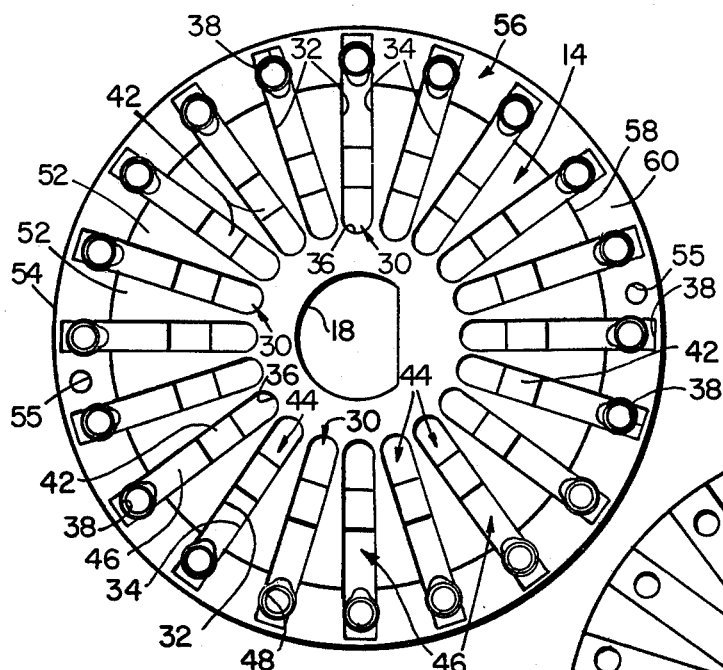
FIG. 3 is a top plan view of the body member of the rotor assembly shown in FIG. 1.

As indicated in FIGS. 1-3, a circumferential array of twenty radially extending cuvette chambers 30 is formed in base member 14. Each cuvette chamber has a maximum capacity of about 400 microliters, a width of slightly less than $\frac{1}{2}$ centimeter between side walls 32, 34, a length of about $3\frac{1}{2}$ centimeters between curved inner wall 36 and outer wall 38, and a planar bottom surface 40. In each cuvette 30 is ramp structure 42 that has a radial length of about six millimeters and a height of about four millimeters and divides the cuvette 30 into an inner chamber 44 and an outer chamber 46. Adjacent the outer end of the bottom wall of each chamber 46 is circular opening 48 in which a Pyrex glass window 50 is seated and bonded. Body member 14 is made of a suitable dimensionally stable, corrosion resistant material such as titanium, stainless steel, diallylphthlate or an epoxy resin.

Figure 4:
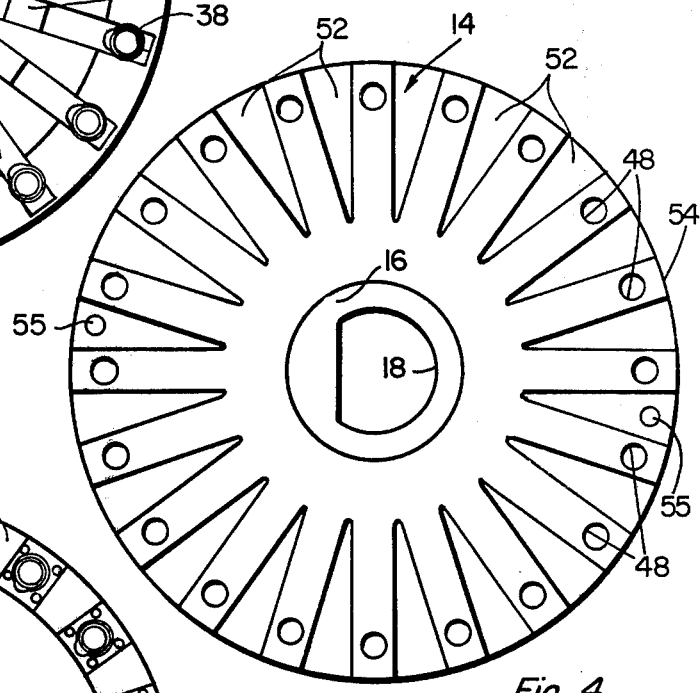
FIG. 4 is a bottom plan view of the body member.

Adjacent cuvettes 30 are interconnected by triangular-shaped webs 52 that extend to annular rim portion 54. As indicated in FIGS. 3 and 4, two pilot holes 55 are in rim 54. An annular recess 56 (about $1\frac{1}{2}$ millimeters in depth and about one centimeter in radial width) is located at the outer periphery of base 14 and has a vertical surface 58 and a planar seating surface 60.

Figure 5:
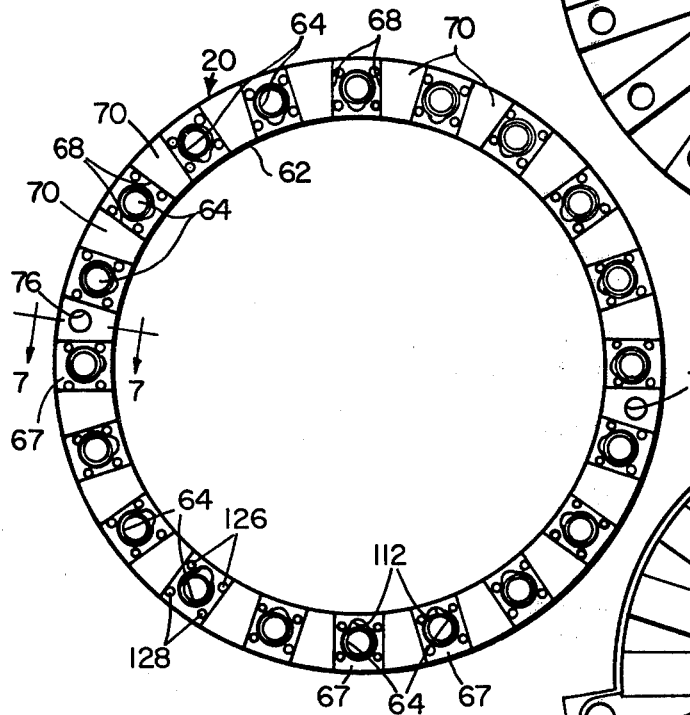
FIG. 5 is a bottom plan view of the ring member of the rotor assembly shown in FIG. 1.

Seated in, and bonded to surfaces 58, 60 of recess 56 is ring 20 (FIG. 5) that is preferably although not necessarily manufactured of the same material as base 14. Ring 20 has an internal diameter of about $8\frac{1}{4}$ centimeters, an external diameter of about ten centimeters, and a thickness of about $1\frac{1}{2}$ millimeters. When ring 20 is seated in recess 56, there is a gap between the inner peripheral surface 62 of ring 20 and vertical recess surfaces 58 that is about 0.1 millimeter in width. Ring 20 has twenty equally spaced circular openings 64 in which a Pyrex or quartz window 66 is seated and bonded. Formed in the lower surface of ring 20 at each opening 64 is a recess defined by planar surface 67 and bounding side walls 68 that has a depth of about 0.2 millimeter and a width of about eight millimeters. The land surfaces 70 between recess side walls 68 seat in direct contact with surfaces 60 of the base when ring 20 is assembled on base 14.

Figure 6:
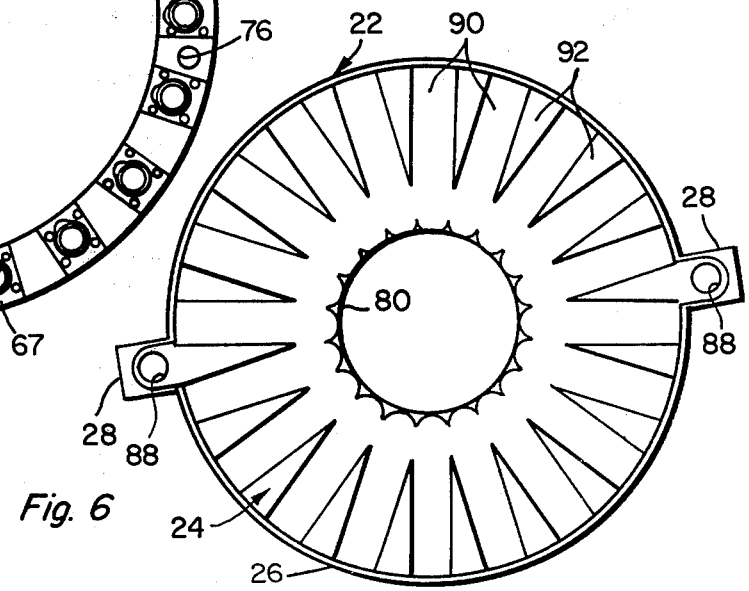
FIG. 6 is a bottom plan view of the cover member of the rotor assembly shown in FIG. 1.

Cover 22 (FIG. 6) includes a stainless steel pressure plate 26 that has an outer diameter of about nine centimeters, a central opening 80 of about three centimeters in diameter and tabs 28, each of which has a pilot aperture 88. Bonded to pressure plate 26 is a silicone rubber gasket 24 (of about ten durometer ShoreA) in which is formed rectangular smooth surfaced seal regions 90, each of which has a width of about six millimeters and projects above adjacent triangular recesses 92 about $\frac{1}{2}$ millimeter.

Figure 8:
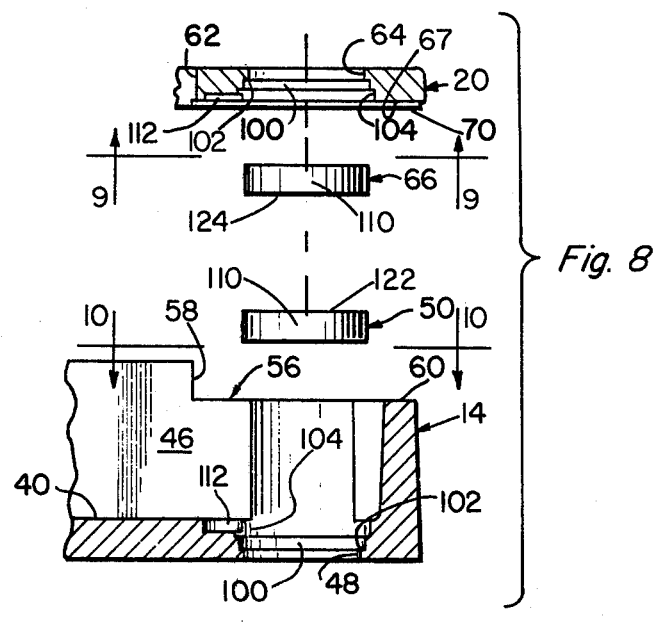
FIG. 8 is an exploded view of optical path defining portions of the body and ring members.
Figures 9, 10:
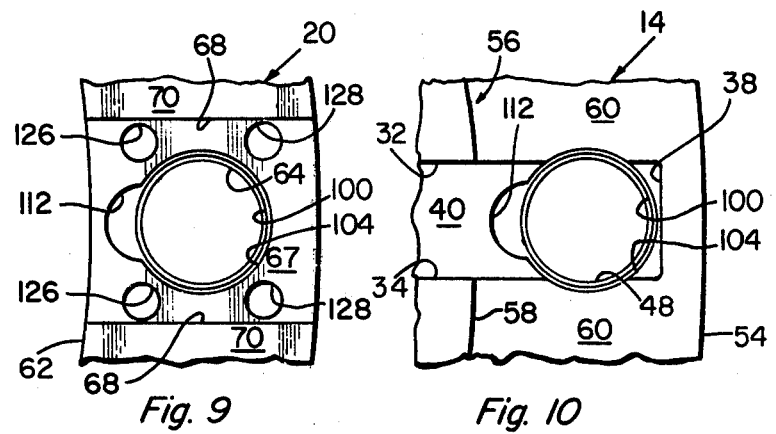
FIG. 9 is a plan view taken along the line 9—9 of FIG. 8 of a portion of the ring member.
FIG. 10 is a plan view taken along the line 10—10 of FIG. 8 of a portion of the body member showing the outer portion of one of the cuvettes and corresponding to the portion of the ring member shown in FIG. 9.

Each Pyrex window 50, 66 is bonded to its support member (base 14 or ring 20) in similar manner. With reference to FIG. 8, each window 50, 66 has a diameter of five millimeters and a thickness of one millimeter. Each opening 48 in base 14 and each opening 64 in ring 20 has a diameter of about 4.7 millimeters. Cylindrical surface 100, concentric with opening 48 (64), is about 5.1 millimeters in diameter and defines a planar support lip surface 102. A second concentric cylindrical surface 104 (of about 5.5 millimeters diameter and about $\frac{1}{2}$ millimeter height) extends downwardly from floor 40 of chamber 46 (or surface 70 of ring 20). Each window 50, 66 is seated on support lip 102 and centered by cylindrical wall 100 so that an annular capillary channel about $\frac{1}{4}$ millimeter in width is defined by the peripheral surface 110 of window 50 (66) and cylindrical wall 104. A semi-circular well or reservoir 112 having a depth of about 0.4 millimeter communicates with that capillary channel.

Figure 12:
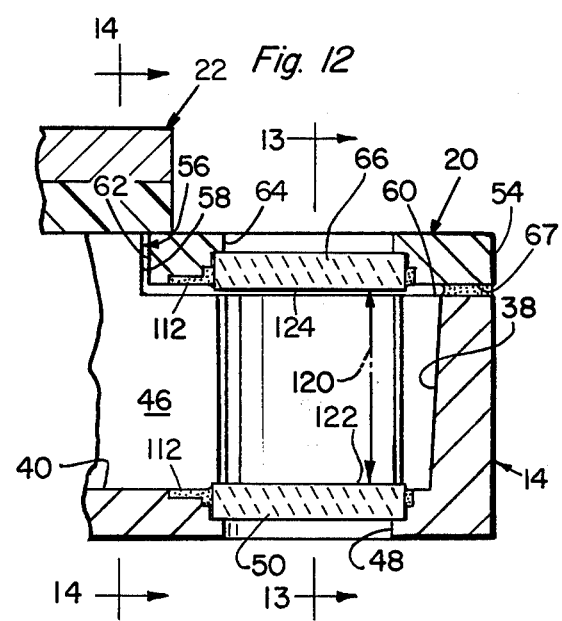
FIG. 12 is an enlarged sectional view showing the optical path in a cuvette.
Figure 13:
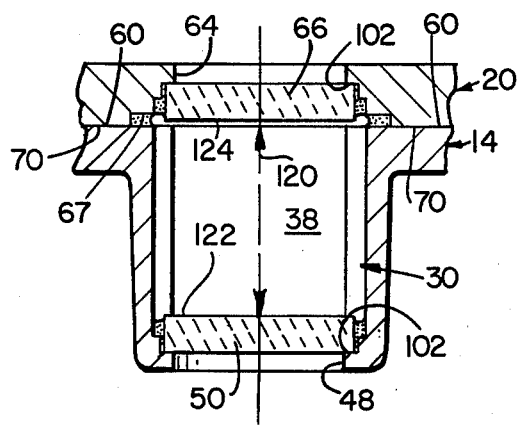
FIG. 13 is a sectional view taken along the line 13—13 of FIG. 12.
Figure 14:
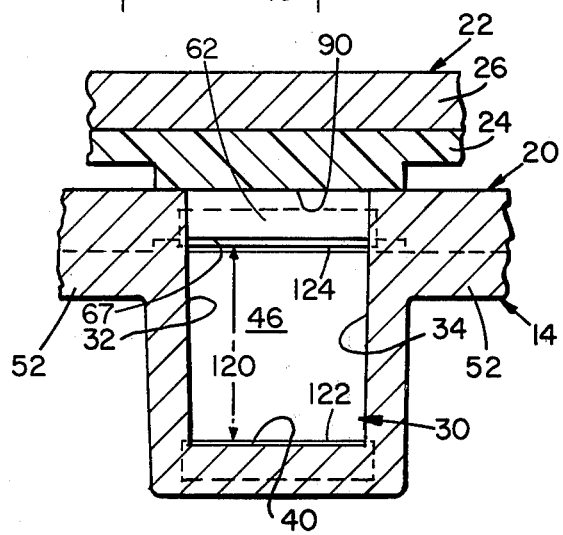
FIG. 14 is a sectional view taken along the line 14—14 of FIG. 12.
Figure 11:
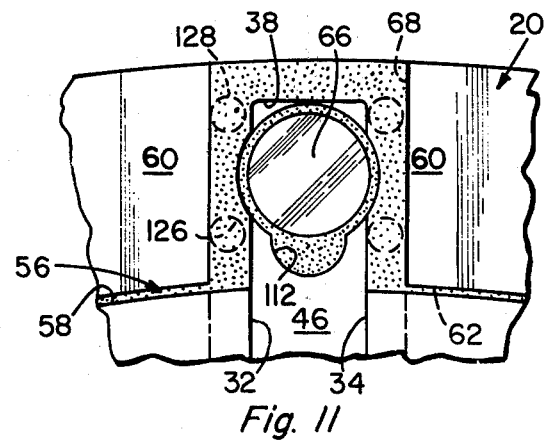
FIG. 11 is a diagrammatic plan view, similar to FIG. 10, showing the location of bonding materials.

A suitable epoxy resin (e.g. Ren RP-4015) is used to bond windows 50, 66 to base 14 and ring 20. Each window is loaded into a corresponding opening 48, 64 with a vacuum pick up pencil assembly so that it is seated on the reference surface of support lip 102. Reservoir well 112 is filled with epoxy using a syringe and the epoxy is allowed to flow around the annular capillary channel. The base 14 or ring 20, as the case may be, is transferred to a heating surface set at about 130° F. which lowers the viscosity of the epoxy so that it flows more easily. Well 112 is filled again with the epoxy sealant (taking care not to fill above the glass surface) until the annular capillary channel is completely filled with epoxy as indicated in FIGS. 11-13. The unit with its twenty epoxy bonded windows (after curing) has bond surfaces that are smooth and corrosion resistant, with the interior surface 122, 124 of each optical window precisely located relative to its reference lip surface 102, free of epoxy and easily cleaned.

Figure 7:
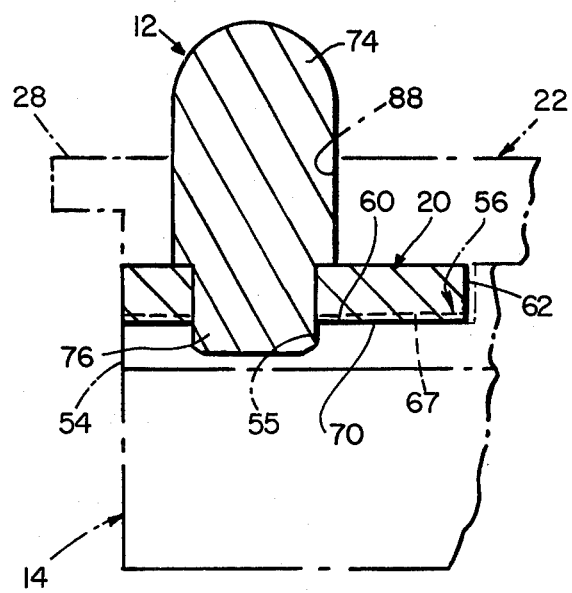
FIG. 7 is an enlarged sectional view of a pilot pin structure employed in the rotor assembly.

After windows 50, 66 have been epoxy bonded to base 14 and ring 20 respectively, ring 20 is piloted onto base 14 by depending pilot pins 76 (FIG. 7) and pilot holes 52, with ring surfaces 70 seated on reference surfaces 60 of the annular recess 56. In that position, windows 66 are in proper alignment with windows 50, and the length of the optical path 120 between the adjacent surfaces 122, 124 of windows 50, 66 is established with precision due to the direct seating of the four components of the optical array of accurately dimensioned reference surfaces 60, 70, and 102, and the accurately dimensioned thickness of optical discs 50, 66. After ring 20 is clamped on base 14, a suitable epoxy resin (e.g., Formulated Resins PR-2020) is dispensed with a syringe, first filling the two (1.5 millimeter diameter) inner reservoir holes 126 adjacent each aperture 64, then filling the outer reservoir holes 128, the epoxy flowing into the 0.2 millimeter wide capillary channel at the outer periphery between base recess surface 60 and ring recess surface 67 between edge surfaces 68. The epoxy resin flows through the capillary channels as indicated in FIG. 11, the reservoir holes 126, 128 being refilled as necessary so that the capillary channels are completely filled. Epoxy resin is also flowed into the vertical channel gaps between base recess surface 58 and the inner peripheral surface 62 of the ring and into the peripheral 0.2 millimeter channel regions (twenty places) around the rim of the rotor. In this condition a continuous seal of epoxy fills the capillary channels between the base 14 and ring 20, as indicated by stippling in FIG. 11, to provide a seal at the outer end of each chamber 46. The epoxy resin seals are then allowed to completely cure.

Figure 15:
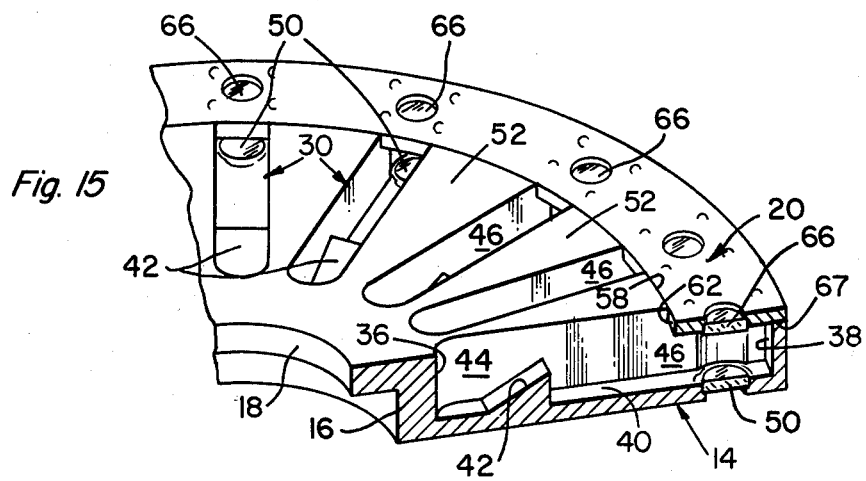
FIG. 15 is a perspective view of a portion of the assembled rotor.

Thus, an optical path 120 of accurately defined length between windows 50 and 66 is defined at the outer end of each of the twenty reaction chambers 46 with the ring structure 20 extending inwardly less than ½ the length of reaction chamber 46 as shown in FIGS. 2 and 15.

Figure 16:
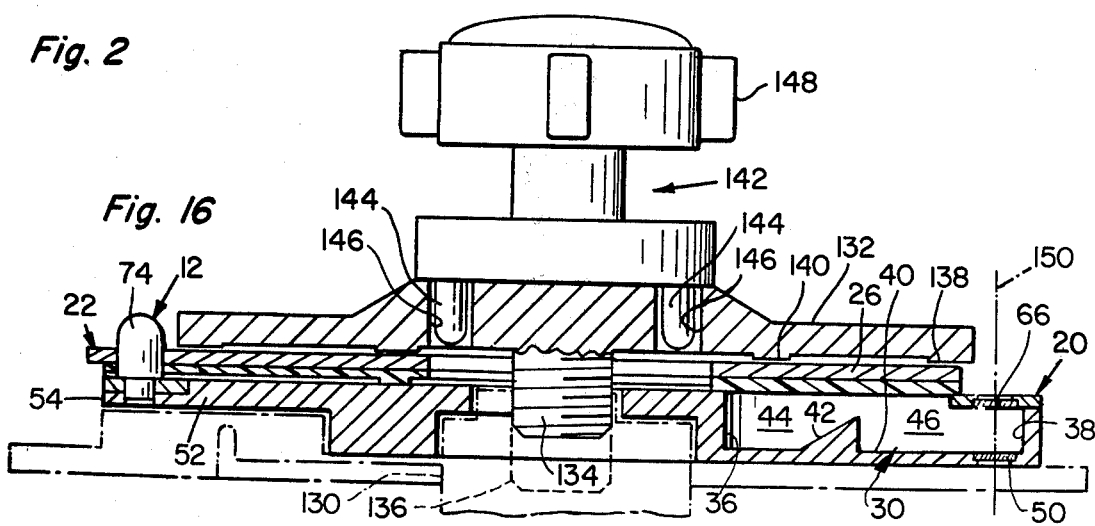
FIG. 16 is a view showing the rotor assembly (in section similar to FIG. 2) mounted on an analytical instrument.

In use, each cuvette chamber 44, 46 is loaded with appropriate reagent and sample materials in conventional manner, and then cover 22 is seated on the rotor body with upstanding pilot post portion 74 engaging cover apertures 88 to properly locate gasket sealing surfaces 90 over the margins of the open tops of the cuvettes as shown in FIG. 2. The covered rotor is then placed on the rotor drive 130 of the centrifugal analyzer as shown in FIG. 16 and secured in place with flanged aluminum seal nut 132 that has a threaded stub shaft 134 that is received into threaded recess 136 in the rotor drive 130. Annular lands 138, 140 seat on pressure plate 26 and concentrate clamping pressure at the inner and outer margins of the gasket seal areas 90. Torque wrench 142 has pins 144 which engage recesses 146 in seal nut 132. Rotation of wrench 142 by means of handle 148 torques cover 22 to seal the cuvette chambers with a force of about fifteen inch pounds. The handle 148 is then removed.

The analytical sequence is then initiated with the rotor being accelerated to 4000 rpm during a preliminary run to flow reactant materials contained in the inner compartments 44 outwardly across ramps 42 into the outer compartments 46 for mixing. The rotational speed of the rotor is then reduced and photometric measurements are made along the optical axis 150.

After the analyses have been completed, the rotor assembly is removed from the centrifugal analyzer for cleaning. After cover assembly 22 is removed, the open cuvette chambers 30 in the body assembly are readily accessible for cleaning and drying. In a manual cleaning procedure, cover 22 is removed, and rinsed with denatured alcohol and distilled water. All of the cavity chambers 44 and 46 of the rotor body are flooded with a free flow of distilled water. During this flooding, a lateral motion of the rotor forces water up into the ends of the cuvette chambers 46. Shaking the rotor removes water from the cuvette chambers. The chambers are then flooded with denatured alcohol using a squeeze bottle and the denatured alcohol removed from the rotor by shaking. For a final rinse, the chambers are again flooded with distilled water. Using an air supply with a secondary filtration system and an air pressure of about 7-10 psi, an air nozzle is directed into the cuvettes to remove water and to dry the window surfaces and other inside surfaces of the cuvette chambers. If necessary, the optical windows may be lightly wiped, using techniques conventional for optical surfaces. An optional further drying step is to place the rotor body and cover assembly components in a non-recirculating type oven preset at a temperature of about 50° C. for about one-half hour. After drying, the rotor components are placed in dust free storage compartments.

The invention provides an improved, reusable, multicuvette analytical rotor assembly whose optical path length is accurately maintained which is suitable for use in precision clinical analysis and which is resistant to chemical attack from chemical reagents that range from strong acids (such as used in a phosphorus analysis), and strong bases (such as are used in total protein and creatinine analysis). The bonding agents have sufficient bond strength to withstand the centrifugal forces to which the rotor is subjected, chemical attack from the reagent materials and the cleaning operation. The rotor is capable of sealing and analyzing sample volumes of 3-90 microliters size range, is compact, is easily loaded with reagent and sample materials, and is easily cleaned for reuse.

While a particular embodiment of the invention has been shown and described, various modifications thereof will be apparent to those skilled in the art, and therefore it is not intended that the invention be limited to the disclosed embodiment or to details thereof and departures may be made therefrom within the spirit and scope of the invention.

What is claimed is:

1. A multicuvette rotor assembly for use in a clinical chemistry analyzer of the centrifugal type comprising
a body member that defines a circumferential array of spaced radially extending recesses, with divider structure in each recess to define a first chamber and a second chamber radially outward from said first chamber, said body member having a series of radially extending reference surface areas extending around the periphery thereof, a circumferential array of first optical windows in the base of said body member, the upper surface of each said first optical window being parallel to said series of reference surface areas, a ring member having a circumferential array of second optical windows in said ring member and a series of mating reference surface areas, said series of mating reference surface areas corresponding to and seated in direct contact engagement with said reference surface areas of said body member such that the inner peripheral edge of said ring member is located radially outwardly of the middle of said second chambers, the lower surface of each said second optical window being parallel to said mating reference surface areas, and in alignment with said first optical windows such that each pair of opposed aligned surfaces of corresponding first and second optical windows are parallel to one another and define an optical path of precise and stable path length, and a cover member that has sealing surfaces for engagement with the edges of the recesses of the body member and the inner peripheral edge of the ring member such that said cover member encloses and seals said recesses to retain reagent and sample material to be analyzed within said chambers.

2. The assembly of claim 1 and further including structure defining a channel of capillary dimension adjacent said engaged reference surfaces, and a bonding agent in said channel that provides a smooth surfaced, sturdy bond between said base and ring members.

3. The assembly of claim 1 wherein each said recess has an open top and said inner peripheral surface of said ring member defines the outer margin of the open top of each said recess, and said cover member has a soft and compliant surface for sealing engagement with upper surfaces of said ring and body members to sealingly enclose said cuvette chambers.

4. The assembly of claim 1 wherein said body and said ring members each have a circumferential array of apertures therein, said apertures in said body member being aligned with corresponding apertures in said ring member, a support surface in each said aperture, each said support surface being parallel to and offset a predetermined distance from the reference surface of that member, an optical window member in each said aperture seated on said support surface so that its upper surface is offset a predetermined distance from the reference surface, the peripheral surface of each said optical window member being spaced from the adjacent aperture surface such that an annular channel of capillary dimension is defined between said peripheral and adjacent surfaces, and a bonding agent in each said annular channel that provides a smooth surfaced, sturdy bond between said peripheral surface of said optical window member and said adjacent aperture surface.

5. An assembly for securing two members together in precise dimensional relation comprising first and second members, each said member having a reference surface, said reference surfaces being in direct and mating engagement, a channel of capillary dimension between said first and second members adjacent said reference surfaces, and a bonding agent in said channel that provides a sturdy bond between said first and second members, said bond having a smooth external surface at the edge of said channel.

6. The assembly of claim 5 wherein each said reference surface is planar and each said member has an aperture therein, said apertures being aligned with one another, a support surface in each said aperture, each said support surface being parallel to and offset a predetermined distance from the reference surface of that member, a reference member in each said aperture, each said reference member having parallel upper and lower surfaces and being seated on said support surface so that its upper surface is offset a predetermined distance from the reference surface, the peripheral surface of each said reference member being spaced from the adjacent aperture surface such that an annular channel of capillary dimension is defined between said peripheral and adjacent surfaces, and a bonding agent in said annular channel that provides a smooth surfaced, sturdy bond between said peripheral and adjacent surfaces, the opposed surfaces of said reference members being disposed parallel to one another in a precise and stable dimensional relationship.

7. The assembly of claim 6 wherein each said reference member is an optical window.

8. An analysis cuvette assembly for use in an analytical system comprising first and second members that define an analytical chamber therebetween, each said member having a planar reference surface, said reference surfaces being in direct and mating engagement, a channel of capillary dimension between said first and second members adjacent said reference surfaces, a flowable bonding agent in said channel that provides a smooth surfaced, sturdy bond between said first and second members, each said member having a wall with an aperture therein, said apertures being aligned with one another, a support surface in each said aperture, each said support surface being parallel to and offset a predetermined distance from the reference surface of that member, an optical window in each said aperture seated on said support surface so that its upper surface is offset a predetermined distance from the reference surface, the peripheral surface of each said optical window being spaced from the adjacent aperture surface such that an annular channel of capillary dimension is defined between said peripheral and adjacent surfaces, and a flowable bonding agent in said annular channel that provides a smooth surfaced, sturdy bond between said peripheral and adjacent surfaces, the opposed surfaces of said optical windows being parallel to one another and defining an optical path of precise and stable path length.

9. The assembly of any one of claims 2 and 4–8 wherein said bonding agent has viscosity and surface tension characteristics such that said bonding agent fills but does not flow out of said channels of capillary dimension.

10. The assembly of any one of claims 2 and 4-8 and further including a supply reservoir region in flow communication with each said capillary channel for receiving said bonding agent for flow into said capillary channel.

11. The assembly of any one of claims 2 and 4-8 wherein each said channel of capillary dimension has a width of less than 0.3 millimeter and said bonding agent is an epoxy resin.

12. The assembly of claim 1 wherein said body member has an annular recess that extends around the periphery of said body member and that defines said series of radially extending reference surface areas, and said ring member is seated in said annular recess so that its upper surface is in the same plane as the upper surface of said body member.

13. The assembly of claim 12 wherein said ring member has a series of spaced recesses disposed around said ring member between said mating reference surfaces, said spaced recesses defining, with opposed surfaces of said body member, a series of channels of capillary dimension adjacent said engaged reference surfaces, and bonding material in said channels provides a smooth surfaced, sturdy bond between said base and ring members.

14. The assembly of claim 13 and further including reservoir apertures in said ring in communication with said spaced recesses.

15. The assembly of claim 14 wherein each said recess has an open top and said inner peripheral surface of said ring member defines the outer margin of the open top of each said recess, and said cover member includes a pressure plate member and a gasket member bonded to said pressure plate member, said gasket member having a soft and compliant surface for sealing engagement with upper surfaces of said ring and base members to sealingly enclose said cuvette chambers.

16. The assembly of claim 15 wherein said body and said ring members each have a circumferential array of apertures therein, said apertures in said body member being aligned with corresponding apertures in said ring member, a support surface in each said aperture, each said support surface being parallel to and offset a predetermined distance from the reference surface of that member, an optical window member in each said aperture seated on said support surface so that its upper surface is offset a predetermined distance from the reference surface, the peripheral surface of each said optical window member being spaced from the adjacent aperture surface such that an annular channel of capillary dimension is defined between said peripheral and adjacent surfaces, and a bonding agent in each said annular channel that provides a smooth surfaced, sturdy bond between said peripheral surface of said optical window member and said adjacent aperture surface.

17. The assembly of claim 16 wherein said bonding agent is an epoxy resin, each said channel of capillary dimension has a width of less than 0.3 millimeter, and further including a supply reservoir region in flow communication with each said capillary channel for receiving said epoxy resin bonding agent for flow into and to fill but not flow out of said capillary channels.

* * * * *